United States Patent
Porro et al.

(10) Patent No.: US 12,324,994 B2
(45) Date of Patent: Jun. 10, 2025

(54) STRIPPER WITH BOTTOM CHAMBER

(71) Applicant: Yara International ASA, Oslo (NO)

(72) Inventors: Lino Giovanni Porro, Etterbeek (BE); Adrian Bynes, Wondelgem (BE)

(73) Assignee: Yara International ASA, Oslo (NO)

( * ) Notice: Subject to any disclaimer, the term of this patent is extended or adjusted under 35 U.S.C. 154(b) by 228 days.

(21) Appl. No.: 18/025,758

(22) PCT Filed: Oct. 8, 2021

(86) PCT No.: PCT/EP2021/077806
§ 371 (c)(1),
(2) Date: Mar. 10, 2023

(87) PCT Pub. No.: WO2022/074174
PCT Pub. Date: Apr. 14, 2022

(65) Prior Publication Data
US 2023/0347258 A1    Nov. 2, 2023

(30) Foreign Application Priority Data

Oct. 8, 2020 (EP) .................................. 20200839

(51) Int. Cl.
| | |
|---|---|
| *B01D 1/06* | (2006.01) |
| *B01D 1/30* | (2006.01) |
| *B01D 19/00* | (2006.01) |
| *B01J 4/00* | (2006.01) |
| *B01J 19/00* | (2006.01) |
| *C07C 273/04* | (2006.01) |
| *C07C 273/16* | (2006.01) |

(52) U.S. Cl.
CPC .............. *B01D 1/30* (2013.01); *B01D 1/065* (2013.01); *B01D 19/0021* (2013.01); *B01J 4/005* (2013.01); *B01J 4/008* (2013.01); *B01J 19/006* (2013.01); *C07C 273/04* (2013.01); *C07C 273/16* (2013.01); *B01J 2204/005* (2013.01)

(58) Field of Classification Search
CPC . B01D 1/06; B01D 1/065; B01D 1/08; B01D 1/10; B01D 1/12; C07C 273/04; C07C 273/14; C07C 273/16
USPC .............................. 159/27.1, 27.3, 27.4, 47.2
See application file for complete search history.

(56) References Cited

U.S. PATENT DOCUMENTS

| | | | |
|---|---|---|---|
| 1,087,409 A | * | 2/1914 | Tiemann .................. B01D 1/08 |
| | | | 159/27.5 |
| 2,696,465 A | | 12/1954 | Kittredge |
| (Continued) | | | |

FOREIGN PATENT DOCUMENTS

| | | | | |
|---|---|---|---|---|
| DE | 2704116 A | * | 2/1978 | ........... B01D 9/0022 |
| DE | 2808923 B1 | | 7/1979 | |
| (Continued) | | | | |

OTHER PUBLICATIONS

PE2E English language abstract of DE 2704116 A.*
(Continued)

*Primary Examiner* — Jonathan Luke Pilcher
(74) *Attorney, Agent, or Firm* — Dilworth IP, LLC

(57) ABSTRACT

A bottom chamber of a stripper (or bottom liquid holder) including a vortex breaker, a blocking plate and a guiding plate. A stripper, a urea HP stripper, a urea plant, a method for operating a stripper and a method for producing a solid, particulate urea-based composition.

17 Claims, 1 Drawing Sheet

(56) References Cited

U.S. PATENT DOCUMENTS

| | | | | |
|---|---|---|---|---|
| 2,897,147 | A * | 7/1959 | Lely | B01D 3/30 |
| | | | | 196/114 |
| 4,810,327 | A * | 3/1989 | Norrmen | B01D 1/065 |
| | | | | 159/13.4 |
| 7,311,746 | B2 * | 12/2007 | Stell | B01D 19/0036 |
| | | | | 55/459.1 |
| 7,588,666 | B2 * | 9/2009 | Saifutdinov | B01D 1/065 |
| | | | | 203/1 |
| 8,286,952 | B2 * | 10/2012 | Lee | B01F 25/10 |
| | | | | 261/109 |
| 9,410,750 | B1 * | 8/2016 | Kurukchi | B01D 3/18 |
| 9,677,830 | B2 * | 6/2017 | Kurukchi | F28F 25/08 |
| 9,694,334 | B2 | 7/2017 | Minola | |
| 2004/0028578 | A1 | 2/2004 | Zardi | |
| 2005/0065374 | A1 | 3/2005 | Pennino | |
| 2005/0224333 | A1 | 10/2005 | Saifutdinov | |
| 2024/0208897 | A1 * | 6/2024 | Beretti | B01D 19/0015 |

FOREIGN PATENT DOCUMENTS

| | | | | |
|---|---|---|---|---|
| EP | 0356537 | A1 | 3/1990 | |
| EP | 3513871 | A1 | 7/2019 | |
| GB | 1196493 | A | 6/1970 | |
| RU | 2275355 | C2 | 4/2006 | |
| RU | 2372327 | C2 | 11/2009 | |
| SU | 993967 | A1 | 2/1983 | |
| SU | 1428398 | A1 * | 10/1988 | B01D 1/065 |

OTHER PUBLICATIONS

PE2E translation of SU 1428398 A1.*
International Search Report and Written Opinion issued in App. No. PCT/EP2021/077806, mailing date Jan. 31, 2022, 14 pages.
Extended European Search Report issued in App. No. EP20200839, dated Apr. 1, 2021, 7 pages.
Office Action and Search Report received for Russian Application No. 2023108780, mailed on Feb. 19, 2025, 16 pages (8 pages of original office action and 8 pages of English Translation).

* cited by examiner

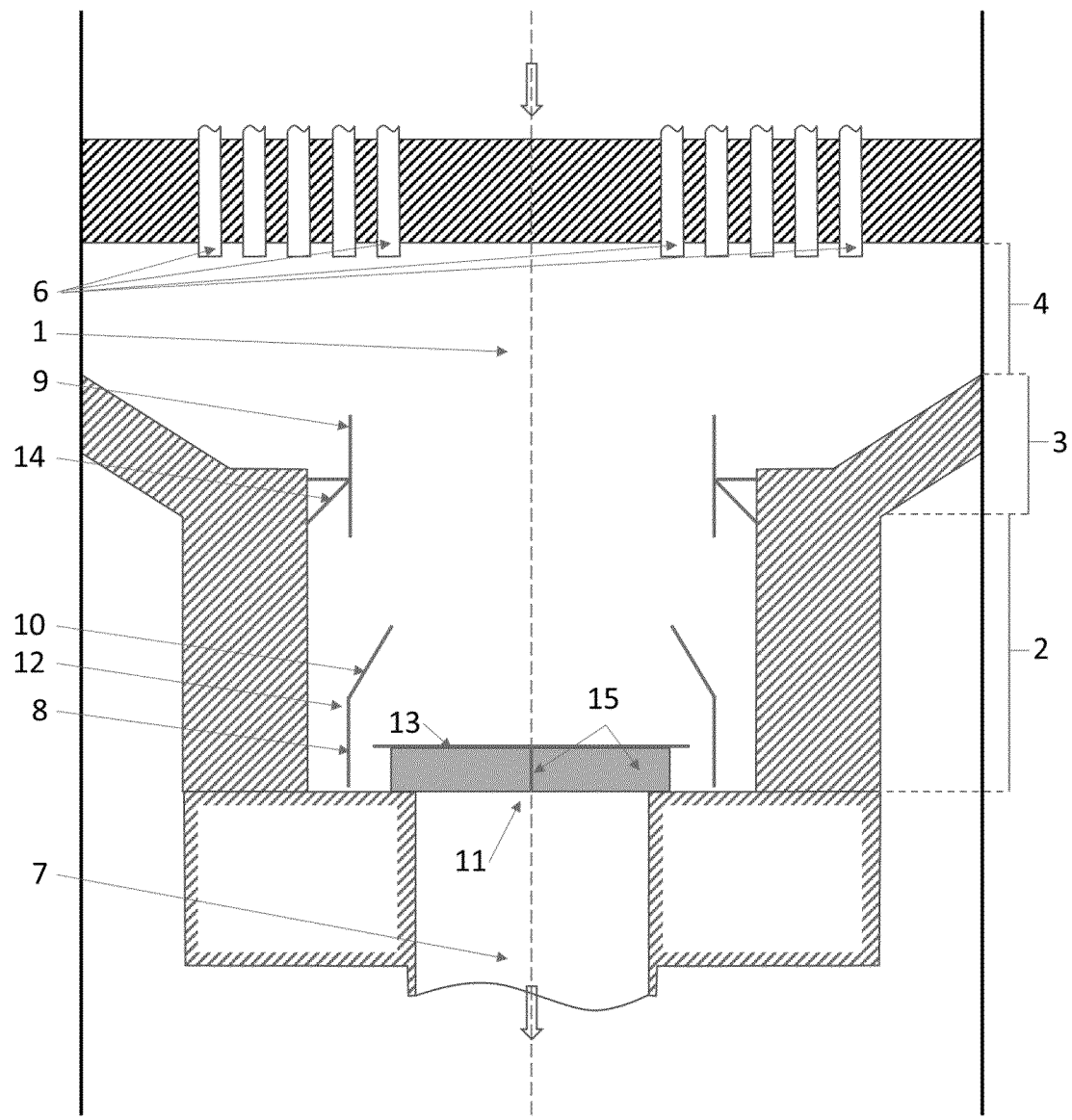

US 12,324,994 B2

STRIPPER WITH BOTTOM CHAMBER

FIELD OF THE INVENTION

The present disclosure is related to the field of chemical manufacturing, in particular to the field of strippers.

BACKGROUND OF THE INVENTION

A stripper is a device used in the manufacturing of chemicals to remove gases or a compound that may decompose into gases upon heating from a liquid solution. A typical stripper comprises a top part or top chamber comprising an inlet for the liquid solution to be stripped and a gas outlet to recover any gas evaporated from the liquid solution, the top part is fluidly connected to a middle part or middle chamber which comprises a plurality of tubes where the liquid solution forms a falling film, and a bottom part or bottom chamber where the liquid solution depleted of gases is collected.

Urea production plants often comprise a stripper. Urea is one of the most important chemicals industrially produced today, around 200 million tons of urea are produced worldwide every year. Most of it (above 90% of total production) is used as a fertilizer in agriculture as a nitrogen source. Urea is produced by reacting ammonia ($NH_3$) and carbon dioxide ($CO_2$) in a two-step process: first, two molecules of ammonia react with one molecule of carbon dioxide to form ammonium carbamate ($H_2N$—$COONH_4$); secondly, ammonium carbamate, which will be referred to as carbamate in the remainder of this document, decomposes into urea and water. Carbon dioxide and ammonia are mixed under high pressure and high temperature in a container, called a urea reactor.

However, the decomposition of ammonium carbamate into urea and water never goes to completion due to the thermodynamics and kinetics of the reaction, and a urea solution comprising urea, ammonium carbamate, free ammonia, and water is obtained. The urea solution is purified in several steps in order to remove the ammonium carbamate, unreacted ammonia, and water, and obtain a concentrated urea melt. In some of these steps, the ammonium carbamate, herein referred to as carbamate, is forced to decompose back to ammonia and carbon dioxide. Since ammonia and carbon dioxide are gases, it is easy enough to remove these from the urea solution. One important step, to remove an important quantity of carbamate and free ammonia, is performed in a so-called urea high pressure (HP) stripper, working at a pressure very close to the urea reactor. This allows to easily recycle the ammonia and carbon dioxide gases back to the reactor. HP strippers often operate at pressures from 80 to 150 bars. Strippers can also operate at low-pressure (less than 5 bars) or medium-pressure (from 10 to 60 bars). The general design of low-pressure or medium-pressure strippers is identical to HP strippers, but some details such as the materials selected to build it may vary slightly, since they operate under different conditions.

Several types of HP strippers exist according to the process technology: in all of them, a HP urea stripper comprises three parts: a top part or top chamber, where the urea solution rich in carbamate from the urea reactor is injected, a middle part or middle chamber where the urea solution is spread into a plurality of tubes, arranged in bundle, and forming a falling film with a downward flow, and a bottom part or bottom chamber. Heat is provided to the middle part of the HP stripper via condensing steam and heats up the outer surface of the tubes. The urea solution is heated up from a temperature of a range between 160-190° C. (according to the technology) up to a temperature between 165 and 210° C. (according to the technology) and kept under pressure, usually between 130-180 bar (according to the technology). Within the plurality of tubes of the HP stripper, part of the ammonium carbamate is transformed back to its raw materials, ammonia and carbon dioxide, which evaporate from the urea solution, together with some free ammonia. The gases are rising in the center of the tubes and they are collected via a gas outlet located in the top chamber of the urea HP stripper, while the urea solution depleted of carbamate and free ammonia is collected at the bottom of the HP stripper in a container, often called a bottom liquid holder. In some technologies, a stripping gas comprising carbon dioxide and/or ammonia, is introduced in the container with the aim to help the ammonia stripping in the tubes. In some technologies, a small quantity of air is sent to the container to provide oxygen for passivation of stainless steel due to high corrosivity of carbamate.

From the container, the urea solution is sent downstream to further purification steps, working at lower pressure than the HP stripper. It is important to keep the content of residual carbamate and free ammonia under control in the urea solution leaving the HP stripper as well as to avoid that some ammonia and carbon dioxide gases, created by the carbamate decomposition, are escaping in the bottom with the urea solution. Any ammonia and carbon dioxide gases present in the urea solution exiting the HP stripper has to be removed by a downstream step. For that reason, a liquid level is maintained in the bottom chamber of the HP stripper (container). Moreover, the level of liquid in the bottom chamber of the HP stripper shall be kept as low as possible in order to:

Reduce residence time and avoid urea hydrolysis reaction that is decomposing urea back to carbamate and further to ammonia and carbon dioxide; and/or Reduce biuret formation from urea, reaction enhanced by high temperature and residence time.

However, it has been observed that even keeping the liquid level high in the lower cylindrical section of the bottom liquid holder, the urea solution collected at the bottom of the HP stripper may contain some gases, in particular ammonia and/or carbon dioxide. This is highly undesirable as explained above. This there is a need to develop a new type of stripper that prevents this phenomenon from happening.

SUMMARY OF THE INVENTION

In one aspect, the present disclosure provides a stripper device comprising a bottom chamber and the bottom chamber of a stripper device, said bottom chamber comprising a container comprising a lower cylindrical section, an intermediate section and an upper cylindrical section; a plurality of openings located on the top wall of the upper cylindrical section; a liquid outlet located at the bottom of the lower cylindrical section of the container and concentric with the lower cylindrical section of the container; wherein the bottom chamber comprises a vortex breaker comprising a top circular plate parallel with the bottom of the lower cylindrical section, concentric with the liquid outlet and joined to the bottom of lower cylindrical section of the container via one or more vertical plates, wherein the diameter of the top plate is greater than the diameter of the liquid outlet to prevent fluid from falling directly from one or more of the plurality of openings directly into the liquid outlet; a blocking plate for preventing bubbles of gas entrained by fluid falling from the plurality of openings from reaching the liquid outlet, comprising a first cylindrical segment concentric with the liquid outlet and with a diameter greater than the diameter of the vortex breaker, and the height of the first cylindrical section is greater than the height of the vortex breaker, wherein the first cylindrical segment being joined to the bottom of the lower cylindrical section, a second segment joined to the top of the first cylindrical segment and having the shape of a truncated cone pointing upwards, wherein the diameter of the bottom of the second segment is equal to the diameter of the first cylindrical segment, the first cylindrical segment comprises one or more openings, thereby allowing fluid to flow from the wall of the lower cylindrical section to the vortex breaker, and the blocking plate overlaps with the vortex breaker, a guiding plate for guiding fluid falling from the walls of the intermediate outwardly section towards the side walls of the lower cylindrical section, the guiding plate being concentric with the liquid outlet, wherein the diameter of the guiding plate is equal to or greater than the diameter than the blocking plate, but smaller than the diameter of the lower cylindrical section of the container, wherein the guiding plate is located at the junction of the lower cylindrical section and the intermediate section, extending partially in the lower cylindrical section and partially in the intermediate section of the container.

Another aspect of the present disclosure provides a stripper device, particularly a urea HP stripper device, comprising the bottom chamber according to the present disclosure.

In another aspect, the present disclosure provides a method for operating a stripper device according to the present disclosure as a urea HP stripper device, comprising the steps of directing a urea solution comprising urea, carbamate, ammonia and water to the liquid inlet of a urea HP stripper device, and recovering from the liquid outlet a urea solution comprising urea and water, and depleted of carbamate, ammonia and optionally carbon dioxide.

In another aspect, the present disclosure provides the use of a urea stripper according to the present disclosure for removing carbamate from an aqueous solution comprising urea and carbamate.

In another aspect, the present disclosure provides the use of a bottom chamber of urea HP stripper according to the present disclosure for reducing the content in ammonia and carbon dioxide in the liquid withdrawn from the bottom chamber of the stripper via the liquid outlet.

BRIEF DESCRIPTION OF THE FIGURES

The following description of the FIGURE of a specific embodiment of a system according to the present disclosure is only given by way of example and is not intended to limit the present explanation, its application or use. In the FIGURE, identical reference numerals refer to the same or similar parts and features.

FIG. 1 represents a cross-section of an embodiment of the bottom chamber of a urea HP stripper according to the present disclosure.

DETAILED DESCRIPTION OF THE INVENTION

Unless otherwise defined, all terms used in disclosing the invention, including technical and scientific terms, have the meaning as commonly understood by one of ordinary skill in the art to which this invention belongs. By means of further guidance, term definitions are included to better appreciate the teaching of the present invention.

All references cited in this description are hereby deemed to be incorporated in their entirety by way of reference.

As used herein, the following terms have the following meanings:

"A", "an", and "the" as used herein refers to both singular and plural referents unless the context clearly dictates otherwise. By way of example, "a compartment" refers to one or more than one compartment.

"About" as used herein referring to a measurable value such as a parameter, an amount, a temporal duration, and the like, is meant to encompass variations of +/−20% or less, in particular +/−10% or less, more in particular +/−5% or less, even more in particular +/−1% or less, and still more in particular +/−0.1% or less of and from the specified value, in so far such variations are appropriate to perform in the disclosed invention. However, it is to be understood that the value to which the modifier "about" refers is itself also specifically disclosed.

"Comprise", "comprising", and "comprises" and "comprised of" as used herein are synonymous with "include", "including", "includes" or "contain", "containing", "contains" and are inclusive or open-ended terms that specifies the presence of what follows e.g. component and do not exclude or preclude the presence of additional, non-recited components, features, element, members, steps, known in the art or disclosed therein.

"Carbamate" refers to ammonium carbamate, the compound obtained after the reaction two moles of ammonia with one mole of carbon dioxide.

The recitation of numerical ranges by endpoints includes all numbers and fractions subsumed within that range, as well as the recited endpoints.

The expression "weight percent", "% wt" or "weight %", here and throughout the description unless otherwise defined, refers to the relative weight of the respective component based on the overall weight of the formulation.

Within the context of the present application, the terms "stripper" and "stripper device" are used interchangeably. Also within the context of the present application, a stripper device refers to a top-to-bottom stripper device where the liquid solution to be stripper is directed to the top chamber of the stripper device and falls through a plurality of tubes via gravity. The liquid solution is collected in the bottom chamber of the stripper device. The terms "top", "upper", "bottom" and "lower" when it relates to the different features of the device or subsections thereof according to the present disclosure thus refers to the position of said features in the device when operating under normal operating conditions.

In one aspect, the present disclosure provides a stripper device comprising a bottom chamber and the bottom chamber of such a stripper device, the bottom chamber comprising a container comprising a lower cylindrical section, an intermediate section and an upper cylindrical section; a plurality of openings located on the top wall of the upper cylindrical section; a liquid outlet located at the bottom of the lower cylindrical section of the container and concentric with the lower cylindrical section of the container; wherein the bottom chamber comprises a vortex breaker comprising a top circular plate parallel with the bottom of the lower cylindrical section, concentric with the liquid outlet and joined to the bottom of lower cylindrical section of the container via one or more vertical plates, wherein the diameter of the top plate is greater than the diameter of the liquid outlet to prevent fluid from falling directly from one or more of the plurality of openings directly into the liquid outlet; a blocking plate for preventing bubbles of gas entrained by fluid falling from the plurality of openings from reaching the liquid outlet, comprising a first cylindrical segment concentric with the liquid outlet and with a diameter greater than the diameter of the vortex breaker, and the height of the first cylindrical section is greater than the height of the vortex breaker, wherein the first cylindrical segment being joined to the bottom of the lower cylindrical section, a second segment joined to the top of the first cylindrical segment and having the shape of a truncated cone pointing upwards, wherein the diameter of the bottom of the second segment is equal to the diameter of the first cylindrical segment, the first cylindrical segment comprises one or more openings, thereby allowing fluid to flow from the wall of the lower cylindrical section to the vortex breaker, and the blocking plate overlaps with the vortex breaker, a guiding plate for guiding fluid falling from the walls of the intermediate outwardly section towards the side walls of the lower cylindrical section, the guiding plate being concentric with the liquid outlet, wherein the diameter of the guiding plate is equal to or greater than the diameter than the blocking plate, but smaller than the diameter of the lower cylindrical section of the container, wherein the guiding plate is located at the junction of the lower cylindrical section and the intermediate section, extending partially in the lower cylindrical section and partially in the intermediate section of the container.

The container of the bottom chamber of a stripper comprises three sections: the upper cylindrical section is connected to the chamber of the scrubber comprising the tubes where the solution is heated and stripped of its gaseous components. The intermediate section does not have a constant diameter and connects the upper cylindrical section to the lower cylindrical section. The lower cylindrical section is where the solution is collected from the plurality of tubes and exits the stripper via the liquid outlet.

Under typical operation conditions, a stripper contains an amount of liquid solution located in its bottom section. It is thought that when the liquid, raining from the plurality of tubes into the intermediate section and overflowing into the lower cylindrical section, hits the surface of the liquid solution located in the lower cylindrical section, some of the gas present in the bottom chamber of the stripper is entrained into the solution in the form of gas bubbles. Once the gas is in the solution, it may be collected via the liquid outlet, especially when the residence time of the liquid in the stripper is rather short, typically 10 to 20 seconds in a urea HP stripper. It is thought that an important amount of entrained gas is reaching the liquid outlet, due to the momentum of the liquid solution overflowing from the intermediate section into the central area of the lower cylindrical section. The presence of gas, for example ammonia and/or carbon dioxide, in the liquid solution in the liquid outlet is highly undesirable since these gases are overloading the downstream sections, creating plant upset. Moreover, the gases may usually be recycled, for example in the urea reactor, to increase the yield of the production method.

A first cylindrical plate or blocking plate is installed in the lower cylindrical section of the stripper to avoid liquid solution, overflowing from the intermediate section and reaching the bottom of the lower cylindrical section due to the momentum, coming in contact with the entrance of the vortex breaker, so obliging any gas entrainment to rise up and stay far away from the inlet of the vortex breaker and liquid outlet. The blocking plate is tilted at the top to stop any bubble spreading towards the central section of the lower cylindrical section, when liquid solution overflow is going down. Secondly, a guiding plate is located at the junction of the lower cylindrical section and the intermediate section of the stripper to oblige the liquid solution overflow to stay in the same annular zone created by the blocking plate.

The bottom chamber of a standard stripper device, shaped as a funnel-like a container, comprises a lower cylindrical section, an intermediate section and an upper cylindrical section; a plurality of openings located on the top wall of the upper cylindrical section; and a liquid outlet located at the bottom of the lower cylindrical section of the container and concentric with the lower cylindrical section of the container. At the liquid outlet a vortex breaker is installed. A vortex breaker consists in a plate, with diameter bigger than the liquid outlet and fixed to the bottom via vertical plates and a at certain distance from the liquid outlet In order to decrease the amount of gas present in the liquid solution collected by the liquid outlet, some improvements to a standard stripper were implemented. First, a vortex breaker is located at the bottom of lower cylindrical section of the container. The vortex breaker comprises a top circular plate parallel with the bottom of the lower cylindrical section and concentric with the liquid outlet, wherein the diameter of the top plate is greater than the diameter of the liquid outlet and the top circular plate is fixed to the bottom of the lower cylindrical section via vertical plates. The vortex breaker prevents the formation of a vortex when the liquid solution exits the stripper. The vortex breaker also prevents the solution falling from the tubes located in the center of the stripper from going directly to the liquid outlet of the container. The top circular plate prevents that any gas entrained by the fall of the solution in the center of the container flows directly to the liquid outlet.

In one embodiment, the vortex breaker is fixed to the bottom of the lower cylindrical section via vertical plates arranged in a cross. The vortex breaker comprises a top circular plate and is fixed to the bottom of the lower cylindrical section of the container. The vortex breaker may be joined to the bottom of the lower cylindrical section by one or more vertical plates that allows the liquid solution to flow to the liquid outlet. For example, it may be fixed via vertical plates arranged in a cross, i.e. wherein the vertical plates are joined at the central axis of the liquid outlet and are positioned at 90° to each other, this is a typical design for a vortex breaker.

In one embodiment, the diameter of the top circular plate of the vortex breaker is comprised between 400 and 600 mm, in particular between 500 and 600 mm.

In one embodiment, the diameter of the top circular plate of the vortex breaker is comprised between 100 and 150% of the diameter of the liquid outlet.

In addition, the bottom holder of the HP urea stripper comprises a blocking plate comprising a first cylindrical segment concentric with the liquid outlet and with a diameter greater than the diameter of the vortex breaker, and the height of the first cylindrical section is greater than the height of the vortex breaker, and a second segment joined to the top of the first cylindrical segment and having the shape of a truncated cone pointing upwards, i.e. towards the intermediate section, wherein the diameter of the bottom of the second segment is equal to the diameter of the first cylindrical segment, the first cylindrical segment comprises one or more openings, thereby allowing fluid to flow from the wall of the lower cylindrical section to the vortex breaker, and the blocking plate overlaps with the vortex breaker, meaning that there is a cross-section of the bottom holder that comprises the first cylindrical segment of the blocking plate and vertical plates of the vortex breaker. The main role of the blocking plate is to block the direct flow from the outer region of the lower cylindrical plate towards the liquid outlet. By blocking this flow, the liquid solution and the gas bubbles entrained by the solution have to move upwards towards the top of the blocking plate, and subsequently flowing over the blocking plate. This movement increases the chance that the gas bubbles will leave the liquid solution and not be recovered in the liquid outlet.

The first cylindrical segment of the blocking plate is concentric with the liquid outlet, i.e. the first cylindrical segment of the blocking plate and the liquid outlet share the same central axis, and is joined to the bottom of the lower cylindrical section. The first cylindrical segment of the blocking plate comprises one or more openings or slots near the bottom of the lower cylindrical section, to allow a very small circulation of liquid solution between the wall of the lower cylindrical segment of the container and the liquid outlet. This circulation avoids stagnant liquid which may be a problem if the liquid comprises a corrosive compound, for example carbamate in a urea stripper. There may be 1, or, 2, or 3, or 4, or 5, or 6, or 7, or 8, or 9, or 10, or more slots or opening. The openings may be equally distributed along the perimeter of the first cylindrical segment of the blocking plate, particularly the openings may be in contact with or adjacent to the bottom of the lower cylindrical section of the container. The openings may have any kind of shape, such as a regular polygonal shape, for example a square shape or triangular, or pentagonal shape, or a circular shape or an irregular shape. In one embodiment, the openings have a square shape. The diameter of the openings may be comprised between 1.0 and 5.0 mm, in particular between 1.0 and 4.0 mm, more in particular between 1.0 and 3.0 mm, i.e. small enough to let the urea solution flow, but not the gas bubbles.

In one embodiment, the one or more openings comprised in the first cylindrical segment of the blocking plate have a polygonal shape, in particular a square shape, in particular a square shape wherein a side of the square is comprised between 1 and 10 mm.

In one embodiment, the one or more openings represent 0.1 to 90% of the perimeter of the first cylindrical segment of the blocking plate, i.e. 0.1 to 50% of the perimeter is hollow and allows the fluid to move from the side of the lower cylindrical segment to the vortex breaker. The more area the one or more openings cover, the more fluid will be allowed to move towards the wave breaker which reduces the risk of fluid stagnation. However, this also increases the risk that some gas bubbles will go through the one or more openings and reach the vortex breaker. In one embodiment, the one or more openings represent less than 10%, in particular less than 5.0%, more in particular less than 2.0%, even more in particular less than 1.0% of the perimeter of the first cylindrical segment of the blocking plate. In one embodiment, the combined area of the one or more openings is comprised between 10 and 100 mm$^2$, in particular between 10 and 80 mm$^2$, more in particular between 10 and 70 mm$^2$, even more in particular between 10 and 50 mm$^2$.

The second segment of the first plate is a truncated cone and pointing upwards, i.e. towards the intermediate section of the container. The role of the second segment of the blocking plate is to avoid that gas bubbles, entrained with the urea solution falling from the top, are spreading wider towards the bottom, being able to reach the entrance of the vortex breaker. The truncated cone will stop the flow of the gas bubbles towards the center of the lower cylindrical section of the container, reducing the momentum of the urea solution and gas bubbles will rise up, since they are lighter than the liquid urea solution.

The bottom chamber of a stripper device according to the present disclosure further comprises a guiding plate concentric with the liquid outlet, wherein the diameter of the guiding plate is equal to or greater than the diameter than the blocking plate, but smaller than the diameter of the lower cylindrical section of the container, wherein the guiding plate is located partially in the lower cylindrical section and partially in the intermediate section of the container. Stated differently, the guiding plate is a cylindrical plate extending partially in the lower cylindrical section and partially in the intermediate section of the container. The role of the guiding plate is to prevent the liquid solution, from the intermediate section, from overflowing into the center of the lower cylindrical section bringing entrained gas into the center. The guiding plate guides the liquid solution and the entrained gas along the wall of the lower cylindrical section of the container to increase the distance travelled by the solution and gas and to direct the liquid solution and the entrained gas to the annular section created by the first cylindrical plate. The guiding plate shares the same central axis with the first cylindrical plate and liquid outlet.

In one embodiment, the bottom chamber of a stripper is the bottom chamber of a urea stripper and the liquid solution flowing in the tubes is a urea solution comprising urea, carbamate, ammonia and water. In one embodiment, the bottom chamber of a stripper is the bottom chamber of a urea HP stripper and the liquid solution flowing in the tubes is a urea solution comprising urea, carbamate, ammonia and water.

In one embodiment, the height of cylindrical section of the blocking plate is between 30 and 70%, in particular between 30 and 65%, more in particular between 30 and 60%, of the height of the lower cylindrical section of the container. The higher the first cylindrical plate is, the longer the fluid has to travel to reach the liquid outlet and the higher is the area where the gas entrained in the solution is released after fluid is changing direction. Increasing the distance for the fluid to travel may increase the chances for the gas to escape, but it may also increase the residence time of the liquid solution in the stripper. Increasing the residence time of the liquid solution in the stripper may not be recommended in some cases: for example, in a urea stripper, increasing the residence time of the liquid solution which comprises urea increases the formation of biuret, a by-product resulting from the decomposition of urea under high pressure and high temperature conditions as well as decomposition of urea in raw materials ammonia and carbon dioxide. Biuret is not a desirable product and its formation should be limited as much as possible as well as partial decomposition of urea will reduce urea plant efficiency. So, a compromise may have to be found between the amount of gas collected in the liquid outlet, the amount of biuret present in the composition at the liquid outlet and the amount of urea present in the liquid solution.

In one embodiment, the second section of the blocking plate, i.e. the truncated cone, has an angle deviating from the vertical axis between 15 and 60 degrees and a upper diameter equal to or smaller than the diameter of the top circular plate of the vortex breaker. As mentioned above, the role of the tilted section is to avoid that gas bubbles, entrained with the urea solution falling from the intermediate section of the container, spread towards the vortex breaker. The tilted section will stop the flow of the gas bubbles, reducing the momentum and gas bubbles will rise up being lighter than the liquid.

In one embodiment, the section of the guiding plate extending into the intermediate section is between 100 and 400 mm. The higher this overlap is, the lower is the possibility that urea solution from section is overflowing into the central section of the lower cylindrical section of the container.

The second plate may be attached to the lower cylindrical segment or the intermediate segment by a variety of attaching means, for example via clips or brackets.

In one embodiment, the section of the guiding plate extending into the lower cylindrical section is between 100 and 400 mm. The higher the overlap is, the lower is the possibility of the entrained bubbles gas to spread wide into the lower cylindrical section. The overlap of the guiding plate with the lower cylindrical section directs the liquid solution flow towards the outside of the annular section created by the first cylindrical plate.

In one embodiment, the bottom chamber of the stripper comprises a pipe extending through the wall of the intermediate section or the upper cylindrical segment of the container adapted to receive a mean for determining the level of liquid solution in the stripper, in particular a radioactive source. During operation of a stripper a key parameter is the level of liquid present in the lower cylindrical section of the container. There are a number of means to determine such a level. One of them uses a combination of a radioactive source enclosed in a pipe located in the container in the intermediate section or the upper cylindrical segment of the container, and a detector located under the lower cylindrical section of the container.

In one embodiment, the bottom chamber of the stripper comprises an injection pipe extending through the wall of the container into the intermediate section or the upper cylindrical section for a stripping gas into the container. The stripping gas may comprise ammonia and/or carbon dioxide. The stripping gas is injecting in the bottom holder of the stripper and flows into the plurality of tubes where it comes into contact with the urea solution. The stripping gas increases the evaporation of the gases comprised in the urea solution falling in the plurality of tubes, i.e. ammonia and carbon dioxide, by reducing the partial pressure of ammonia and/or carbon dioxide in the aqueous solution and accelerating its vaporization.

In one embodiment, the diameter of the first cylindrical segment of the blocking plate is comprised between 400 and 900 mm.

In one embodiment, the diameter of the lower cylindrical section of the container is comprised between 0.5 and 1.5 m, in particular between 0.6 and 1.4 m, more in particular between 0.7 and 1.3 m, even more in particular between 0.7 and 1.1 m.

In on embodiment, the height of the lower cylindrical section of the container is comprised between 0.5 and 1.5 m, in particular between 0.7 and 1.4 m, more in particular between 0.8 and 1.3 m, even more in particular between 0.9 and 1.3 m.

In one embodiment, the diameter of the liquid outlet is comprised between 150 and 600 mm, in particular between 170 and 550 mm, more in particular between 180 and 500 mm, even more in particular between 200 and 450 mm, even more in particular between 250 and 400 mm.

In one embodiment, the diameter of the second plate is comprised between 450 and 1100 mm, in particular between 470 and 1050 mm, more in particular between 480 and 1000 mm, even more in particular between 500 and 950 mm, even more in particular between 400 and 900 mm.

In one embodiment, the height of the guiding plate is comprised between 200 and 600 mm, in particular between 250 and 550 mm.

In one embodiment, the intermediate section is outwardly curved. In one embodiment, the intermediate section is a truncated cone pointing downwards, i.e. towards the lower cylindrical section.

In another aspect, the present disclosure provides a stripper comprising a top chamber or distribution chamber, a middle chamber and a bottom chamber as described herein, wherein the top chamber and the middle chamber are joined together and the middle chamber and bottom chamber are also joined together. The top chamber of the stripper comprises a liquid inlet for the liquid solution to be stripped of, a gas outlet to collect gases, and a plurality of openings for receiving the plurality of tubes comprised in the middle chamber of the stripper. The middle chamber comprises a plurality of tubes for guiding the liquid solution from the top chamber to the bottom chamber of the stripper and means for heating up the plurality of tubes. The means for heating up the plurality of tubes may comprise a shell surrounding the plurality of tubes and an inlet for a heating fluid, for example steam, and an outlet for the heating fluid. The plurality of openings in the bottom chamber are configured to receive the plurality of tubes of middle chamber of the stripper device.

In another aspect, the stripper device according to the present disclosure is a urea HP stripper. Accordingly, in another aspect, the present disclosure provides a urea HP stripper comprising a top chamber or distribution chamber, a middle chamber and a bottom chamber as described herein, wherein the top chamber and the middle chamber are joined together and the middle chamber and bottom chamber are also joined together. The top chamber of a urea HP stripper comprises a liquid inlet for the urea solution comprising urea, carbamate, ammonia and water, a gas outlet to collect gases generated from the decomposition of carbamate and heating of the urea solution, and a plurality of openings for receiving the plurality of tubes comprised in the middle chamber of the stripper. The middle chamber comprises a plurality of tubes for guiding the liquid solution from the top chamber to the bottom chamber of the stripper and means for heating up the plurality of tubes. The means for heating up the plurality of tubes may comprise a shell surrounding the plurality of tubes and an inlet for a heating fluid, for example steam, and an outlet for the heating fluid. The plurality of openings in the bottom chamber are configured to receive the plurality of tubes of middle chamber of the stripper device.

The gases collected may comprise ammonia, carbon dioxide and/or water. The top chamber of the urea HP stripper may comprise other devices, such as a distribution device to distribute the urea solution evenly over the plurality of tubes of the middle part. The middle chamber comprises a plurality of tubes for guiding the urea solution from the top chamber to the bottom chamber. The middle chamber may comprise a shell for housing the heating fluid which heats up the plurality of tubes and catalyzes the conversion of carbamate back to ammonia and carbon dioxide. The middle chamber may also comprise baffle plates or rods to reduce the vibrations of the plurality of tubes. The bottom chamber of the urea HP stripper is a bottom chamber according to the present disclosure.

The top, middle and bottom chambers of the HP stripper have the same diameter.

In one embodiment, the urea HP stripper has a diameter between 2.0 and 4.0 m, in particular between 2.1 and 3.9 m, more in particular between 2.3 and 3.7 m, even more in particular between 2.5 and 3.3 m. The greater the diameter of a urea HP stripper is, the more tubes it may comprise in its middle chamber allowing to process more urea solution per unit of time.

In another aspect, the present disclosure provides a urea plant for producing urea comprising a urea HP stripper according to the present disclosure. A urea plant comprises a plurality of devices to transform raw materials, ammonia and carbon dioxide, into a solid, particulate urea-based composition. A urea plant always comprises a urea reactor where the ammonia and carbon dioxide are mixed under high pressure and high temperature and an urea solution comprising urea, carbamate, ammonia and water is produced. In particular, a urea plant for producing urea comprises a synthesis section comprising a urea HP stripper according to the present disclosure, a low-pressure section, and optionally a finishing section.

In another aspect, the present disclosure provides a method for operating a stripper device according to the present disclosure, comprising the steps of a) directing a liquid composition in the liquid inlet of a stripper, in particular a urea HP stripper, according to the present disclosure; and b) collecting a liquid composition depleted of gases from the liquid outlet of the stripper.

In another aspect, the present disclosure provides a method for operating a urea HP stripper device according to the present disclosure, comprising the steps of a) directing a liquid composition comprising urea, carbamate, ammonia and water obtained in the liquid inlet of the urea HP stripper according to the present disclosure; and b) collecting a liquid composition comprising urea, water and depleted of ammonia and carbamate from the liquid outlet of the urea HP stripper.

It is necessary to obtain an aqueous urea solution of high quality, i.e. with a very low amount of contaminants in order to produce a solid, particulate, urea-based composition. Because of the thermodynamics of the reaction to produce urea, it is not possible to obtain a urea solution with high purity at the outlet of a urea reactor. The urea solution always comprises urea, carbamate, ammonia, and water. It is well known that it is possible to force the carbamate to decompose back to its raw materials, ammonia and carbon dioxide, in an apparatus such as a urea HP stripper. Once the stripper has been installed in the production line, the urea solution obtained from the urea reactor, may be injected into the stripper. The pressure and temperature conditions inside the stripper makes the carbamate decompose back to ammonia and carbon dioxide while the urea is having a very low reaction. The ammonia and carbon dioxide are recovered from the gas outlet comprised in the HP stripper and may be recycled to the urea reactor for example. The aqueous urea solution obtained at the liquid outlet of the urea HP stripper may still contain some carbamate, although in much smaller amounts than the solution injected into the stripper.

In another aspect, the present disclosure provides the use of a urea HP stripper according to the present disclosure for removing carbamate from an aqueous solution comprising urea and carbamate.

In another aspect, the present disclosure provides the use of a bottom chamber of urea HP stripper according to the present disclosure for reducing the content in ammonia and carbon dioxide in the liquid withdrawn from the bottom chamber of the stripper via the liquid outlet.

In another aspect, the present disclosure provides a method for producing a solid, particulate urea-based composition comprising the steps of: a) reacting a mixture of ammonia and carbon dioxide in a urea reactor, thereby producing a urea solution comprising urea, carbamate, ammonia, water and optionally carbon dioxide; b) directing the urea solution comprising urea, carbamate, ammonia, water and optionally carbon dioxide obtained in step a) in a urea HP stripper according to the present disclosure; c) collecting a urea solution comprising urea, and water and depleted of ammonia and carbamate from the liquid outlet of the urea HP stripper; d) concentrating the urea solution comprising urea and water obtained in step c), thereby obtaining a concentrated urea aqueous solution; e) transforming the concentrated urea aqueous solution obtained in step d) into a solid, particulate, urea-based composition.

The steps a), b), d) and e) of the method above to produce a solid, particulate urea-based composition are well known in the field of urea production.

In typical operating conditions, the mixture of ammonia and carbon dioxide in the urea reactor is heated up at high temperature under high pressure, see above. Ammonia and carbon dioxide are added in the reactor in such a way that there is always an excess of ammonia compared to carbon dioxide.

The concentrating step d) often provides a urea melt comprising 1.0 to 5.0 weight % of water.

The water content may be adjusted depending on the transforming step.

The transforming step may be done in a variety of equipment known in the field, such as fluidized bed, pan granulator, drum granulator, prilling tower, spherodizer, pugmill and pastillizer.

The method may comprise further steps where required, for example it may be necessary to perform additional steps to remove any one of ammonia, carbamate or carbon dioxide still present in the urea solution obtained in step c) before concentrating the urea solution.

In one embodiment, it may be required to add further components to the urea solution or the concentrated urea solution. The further components may be process additives to improve the production process, such as viscosity-reducing additives, the further components may also be additives to improve the properties of the solid, particulate urea-based composition such as granulation additives, for example an additive comprising urea-formaldehyde.

In another aspect, the present disclosure provides the use of a stripper according to the present disclosure, particularly a urea HP stripper according to the present disclosure, for reducing the content in carbamate, ammonia and carbon dioxide of a solution comprising urea, carbamate, ammonia and water.

Example 1

The drawing in FIG. 1 depicts a cross-section of a bottom chamber of a urea HP stripper according to the present invention. The stripper comprises a container 1 that comprises three sections: an upper cylindrical section 4, an intermediate section 3 and a lower cylindrical section 2. The upper cylindrical section has a diameter of 3.1 m, and the lower cylindrical section 2 has a diameter 1.0 m and a height of 1.1 m. The stripper may comprise between 3500 and 6000 tubes, in connection with a plurality of openings 6 located on the top wall of the upper cylindrical section, the tubes being arranged in a bundle with the exit in the top chamber of the container: the urea solution comprising urea, carbamate, ammonia and water is entering the container via a falling film type regime, while the gases are exiting the container through the same tubes. The stripper comprises a liquid outlet 7 located at the bottom of the lower cylindrical section 2 and is concentric with the lower cylindrical section 2. The diameter of the liquid outlet is 320 mm.

The container comprises two plates, i.e. a guiding plate and a blocking plate. The first cylindrical blocking plate 12 comprises a first cylindric segment 8 concentric with the liquid outlet 7 and with a diameter comprised between 650 and 900 mm, in particular between 650 and 850 mm, and a height comprised between 250 and 500 mm, in particular between 300 and 450 mm. The first cylindrical blocking plate 12 comprises a second segment 10 joined to the top of the first cylindrical segment 8 and having the shape of a truncated cone pointing towards the intermediate section 3, wherein the diameter of the bottom of the second segment 10 is equal to the diameter of the first cylindrical segment 8. The angle of the truncated cone 10 deviates from the vertical by an angle comprised between 15 and 60 degrees, in particular between 30 and 45 degrees. The upper diameter of the second segment 10 is comprised between 400 and 600 mm, in particular between 500 and 600 mm. The first cylindrical segment 8 comprises 2 to 10 openings or holes on its perimeter (not shown here), thereby allowing fluid to flow from the wall of the lower cylindrical section to the vortex breaker. Each hole is a square in contact with the bottom of the lower cylindrical section 2 of the container, wherein each side of the squares measures between 1 and 5.0 mm.

The second plate is cylindrical guiding plate 9. Guiding plate 9 is concentric with the first cylindrical segment 8 of the blocking plate 12 and concentric with the liquid outlet 7, and overlaps with the intermediate section 3, meaning that one section of the guiding plate is entering the intermediate section. The diameter of the guiding plate 9 may be between 650 and 950 mm, but always least equal to the diameter of the first cylindrical segment 8 of the blocking plate 12, but smaller than the diameter of the lower cylindrical section 2 of the container. The guiding plate 9 is located between the end of the intermediate section 3 and the top of the lower cylindrical section 2 of the container. The height of the second plate 9 is comprised between 200 and 600 mm, in particular between 250 and 550 mm. The second plate 9 is attached to the lower cylindrical segment 2 via brackets 14.

The container 1 also comprises a vortex breaker 11 concentric with the liquid outlet 7. The vortex breaker comprises a top circular plate 13 with a dimeter comprised between 400 and 600 mm, in particular between 500 and 600 mm. The diameter of the top plate 13 of the vortex breaker 11 should be smaller than the diameter of the first cylindrical segment 8 of the blocking plate 12 to allow the urea solution to reach the liquid outlet. The vortex breaker is fixed to the bottom of the lower cylindrical section via vertical plates 15 arranged in a cross.

The invention claimed is:

1. A stripper comprising a top chamber comprising a liquid inlet, and a gas outlet, an intermediate chamber comprising a plurality of tubes and a bottom chamber, wherein the bottom chamber comprises a container comprising a lower cylindrical section, an intermediate section and an upper cylindrical section, a plurality of openings located on a top wall of the upper cylindrical section, a liquid outlet located at a bottom of the lower cylindrical section of the container and concentric with the lower cylindrical section of the container; and the plurality of openings are configured to receive the plurality of tubes, wherein the plurality of tubes are configured for guiding a fluid comprising dissolved gases from the top chamber of the stripper to the bottom chamber;
wherein the bottom chamber further comprises
   (i) a vortex breaker joined to the bottom of the lower cylindrical section of the container, the vortex breaker comprising a top circular plate parallel with the bottom of the lower cylindrical section and concentric with the liquid outlet, the top circular plate being fixed to the bottom of the lower cylindrical section via vertical plates arranged in a cross, wherein a diameter of the top circular plate is greater than a diameter of the liquid outlet to prevent fluid from falling directly from one or more of the plurality of openings directly into the liquid outlet;
   (ii) a blocking plate for preventing bubbles of gas entrained by fluid falling from the plurality of openings from reaching the liquid outlet, the blocking plate comprising a first cylindrical segment concentric with the liquid outlet and with a diameter greater than a diameter of the vortex breaker, and a height of the first cylindrical segment being greater than a height of the vortex breaker, said first cylindrical segment being joined to the bottom of the lower cylindrical section, and a second segment joined to a top of the first cylindrical segment and having a shape of a truncated cone pointing upwards, wherein a diameter of a bottom of the second segment is equal to a diameter of the first cylindrical segment, wherein the first cylindrical segment comprises one or more openings, thereby allowing fluid to flow from a wall of the lower cylindrical section to the liquid outlet;
   (iii) a guiding plate for guiding fluid falling from the walls of the intermediate section towards a side wall of the lower cylindrical section, the guiding plate being concentric with the liquid outlet, wherein a diameter of the guiding plate is equal to or greater than a diameter of the blocking plate, but smaller than a diameter of the lower cylindrical section of the container, wherein the guiding plate is located at a junction of the lower cylindrical section and the intermediate section, extending partially in the lower cylindrical section and partially in the intermediate section of the container.

2. The stripper according to claim 1, wherein the height of the first cylindrical segment of blocking plate is between 10 and 50% of a height of the lower cylindrical section of the container.

3. The stripper according to claim 1, wherein the diameter of the top circular plate of the vortex breaker is between 400 and 600 mm.

4. The stripper according to claim 1, wherein the diameter of the first cylindrical segment of the blocking plate is between 400 and 900 mm.

5. The stripper according to claim 1, wherein a height of the guiding plate is between 200 and 600 mm.

6. The stripper according to claim 1, further comprising a pipe extending through a wall of the intermediate section or the upper cylindrical section of the container adapted to receive a means for determining a level of liquid in the bottom chamber of the stripper.

7. The stripper according to claim 6, wherein the means for determining the level of liquid in the bottom chamber of the stripper is a radioactive source.

8. The stripper according to claim 1, further comprising an injection pipe extending through a wall of the container into the intermediate section or the upper cylindrical section for injecting a stripping gas into the bottom chamber.

9. The stripper according to claim 8, wherein the stripping gas comprises carbon dioxide and/or ammonia.

10. The stripper according to claim 1, wherein the one or more openings comprised in the first cylindrical segment of the blocking plate have a polygonal shape.

11. The stripper according to claim 10, wherein the one or more openings have a square shape, wherein a side of the square shape is between 1 and 10 mm in length.

12. A urea plant for producing urea comprising a synthesis section comprising the stripper according to claim 1 as a urea high pressure (HP) stripper and a low-pressure section.

13. The urea plant according to claim 12, further comprising a finishing section.

14. A method for operating the stripper according to claim 1 as a urea HP stripper, comprising steps of a) directing a urea solution comprising urea, carbamate, ammonia and water to the liquid inlet of the urea HP stripper, and b) recovering from the liquid outlet of the bottom chamber of the urea HP stripper a urea solution comprising urea and water, and depleted of carbamate and ammonia.

15. The method according to claim 14, wherein the urea solution further comprises carbon dioxide.

16. A method for operating the stripper according to claim 1 as a urea HP stripper, wherein the method includes producing a solid, particulate urea-based composition, comprising steps of
  a0) reacting a mixture of ammonia and carbon dioxide in a urea reactor, thereby producing a urea solution comprising urea, carbamate, ammonia, and water;
  a) directing the urea solution comprising urea, carbamate, ammonia, and water obtained in step a0) in the urea HP stripper;
  b) collecting a urea solution comprising urea and water, and depleted of ammonia and carbamate from the liquid outlet of the urea HP stripper;
  c) concentrating the urea solution comprising urea and water obtained in step c), thereby obtaining a concentrated urea aqueous solution;
  d) transforming the concentrated urea aqueous solution obtained in step d) into a solid, particulate, urea-based composition.

17. The method according to claim 16, wherein the urea solution further comprises carbon dioxide.

* * * * *